US00PP25403P2

(12) United States Plant Patent
van den Hoogen

(10) Patent No.: US PP25,403 P2
(45) Date of Patent: Mar. 31, 2015

(54) ***CAMPANULA* PLANT NAMED 'ALLGENTITWIST'**

(50) Latin Name: *Campanula glomerata*
Varietal Denomination: Allgentitwist

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 147 days.

(21) Appl. No.: 13/815,457

(22) Filed: Mar. 5, 2013

(51) Int. Cl.
*A01H 5/00* (2006.01)

(52) U.S. Cl.
USPC ..... Plt./414

(58) Field of Classification Search
USPC ..... Plt./414
See application file for complete search history.

*Primary Examiner* — Anne Grunberg
(74) *Attorney, Agent, or Firm* — C. A. Whealy

(57) ABSTRACT

A new and distinct cultivar of *Campanula* plant named 'Allgentitwist' characterized by its broadly upright plant habit; freely basal branching habit; freely and uniformly flowering habit; campanulate-shaped flowers with violet-colored petals and white-colored sepals giving a bi-colored appearance; and good garden performance.

4 Drawing Sheets

Botanical designation: *Campanula glomerata.*
Cultivar denomination: 'ALLGENTITWIST'.

BACKGROUND OF THE INVENTION

The present invention relates to a new and distinct cultivar of *Campanula* plant, botanically known as *Campanula glomerata* and hereinafter referred to by the name 'Allgentitwist'.

The new *Campanula* is a product of a planned breeding program conducted by the Inventor in Cuijk, The Netherlands. The objective of the breeding program is to create new freely flowering *Campanula* plants with attractive inflorescences and good garden performance.

The new *Campanula* plant originated from an open-pollination in Cuijk, The Netherlands during June, 2009 of a proprietary selection of *Campanula glomerata* identified as code number 6-3-21, not patented, as the female, or seed, parent with an unknown selection of *Campanula glomerata* as the male, or pollen, parent. The new *Campanula* was discovered and selected by the Inventor as a single flowering plant from within the progeny of the stated open-pollination grown in a controlled outdoor nursery in Cuijk, The Netherlands in June, 2011.

Asexual reproduction of the new *Campanula* plant by tissue culture in The Netherlands, since July, 2011 has shown that the unique features of this new *Campanula* plant are stable and reproduced true to type in successive generations.

SUMMARY OF THE INVENTION

Plants of the new *Campanula* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Allgentitwist'. These characteristics in combination distinguish 'Allgentitwist' as a new and distinct *Campanula* plant:

1. Broadly upright plant habit.
2. Freely basal branching habit.
3. Freely and uniformly flowering habit.
4. Campanulate-shaped flowers with violet-colored petals and white-colored sepals giving a bi-colored appearance.
5. Good garden performance.

Plants of the new *Campanula* differ from plants of the female parent selection in the following characteristics:

1. Flowers of plants of the new *Campanula* have violet-colored petals whereas flowers of plants of the female parent selection have blue-colored petals.
2. Flowers of plants of the new *Campanula* have white-colored sepals whereas flowers of plants of the female parent selection have green-colored sepals.

Plants of the new *Campanula* can be compared to plants of *Campanula glomerata* 'Allgentibl', disclosed in U.S. Plant patent application Ser. No. 13/694,021. Plants of the new *Campanula* differ primarily from plants of 'Allgentibl' in the following characteristics:

1. Flowers of plants of the new *Campanula* had violet-colored petals whereas flowers of plants of 'Allgentibl' had purple violet-colored petals.
2. Flowers of plants of the new *Campanula* had white-colored sepals whereas flowers of plants of 'Allgentibl' had green-colored sepals.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the colors of the new *Campanula* plant.

The photograph on the first sheet is a side perspective view of a typical flowering plant of 'Allgentitwist' grown in a container.

The photograph on the second sheet is a close-up view of typical leaves of 'Allgentitwist'.

The photograph on the third sheet is a close-up view of typical developing inflorescences of 'Allgentitwist'.

The photograph on the fourth sheet is a close-up view of typical developed inflorescences of 'Allgentitwist'.

DETAILED BOTANICAL DESCRIPTION

Plants used for the aforementioned photographs and following description were grown during the early summer in an outdoor nursery in Cuijk, The Netherlands and under cultural practices typical of commercial production conditions. Plants used for the photographs were grown in 13-cm containers and plants used for the description were grown in ground beds. During the production of the plants, day temperatures ranged from 15° C. to 28° C. and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Campanula glomerata* 'Allgentitwist'.

Parentage:

*Female parent*.—Proprietary selection of *Campanula glomerata* identified as code number 6-3-21, not patented.

*Male parent*.—Unknown selection of *Campanula glomerata*, not patented.

Propagation:

*Type*.—By tissue culture.

*Time to initiate roots, summer*.—About 20 days at 6° C. to 28° C.

*Time to initiate roots, winter*.—About 25 days at 6° C. to 28° C.

*Time to produce a rooted young plant, summer*.—About 30 days at 6° C. to 28° C.

*Time to produce a rooted young plant, winter*.—About 35 days at 6° C. to 28° C.

*Root description*.—Fine, fibrous; white in color.

*Rooting habit*.—Moderately freely branching; medium density.

Plant description:

*Plant and growth habit*.—Herbaceous perennial; broadly upright plant habit; freely basal branching habit with about 15 basal branches developing per plant; moderately vigorous growth habit; campanulate flowers arranged in compound racemes.

*Plant height*.—About 51.5 cm.

*Plant width*.—About 40 cm.

*Basal branch description*.—Aspect: About 5° from vertical. Length: About 42.5 cm. Diameter: About 5 mm. Internode length: About 3.4 cm. Strength: Strong. Texture: Moderately pubescent. Color: Close to 144C to 144D with longitudinal stripes, close to 143B and 144A and strongly tinged with close to 178A to 178B.

Foliage description:

*Arrangement*.—Alternate, simple.

*Length*.—About 11.5 cm.

*Width*.—About 3.3 cm.

*Shape*.—Narrowly ovate to lanceolate.

*Apex*.—Acute.

*Base*.—Attenuate.

*Margin*.—Serrate.

*Texture, upper and lower surfaces*.—Moderately pubescent; rough; slightly rugose.

*Venation pattern*.—Pinnate.

*Color*.—Developing leaves, upper surface: Close to N137A to N137B with irregular marbling, close to 157C to 157D. Developing leaves, lower surface: Close to 137A to 137B with irregular marbling, close to 157C to 157D. Fully developed leaves, upper surface: Close to N137A; occasionally and very slightly with irregular marbling, close to 157A to 157B; venation, between 147D and 148D. Fully developed leaves, lower surface: Close to 147B; venation, close to 144A.

*Petioles*.—Basal leaves, petiolate; upper leaves, sessile. Length: About 4.3 cm. Diameter: About 1.5 mm. Texture, upper and lower surfaces: Sparsely pubescent. Color, upper and lower surfaces: Close to 144C; towards the margins, close to 144A.

Flower description:

*Flower arrangement and shape*.—Single campanulate sessile flowers arranged in axillary and terminal racemes; flowers face mostly upright to slightly outwardly; freely flowering habit with about 22 flowers developing per terminal inflorescence and about ten flowers developing per axillary inflorescence.

*Natural flowering season*.—Plants begin flowering about nine months after planting; in the garden, flowering continuous from late May to early August in The Netherlands.

*Flower longevity on the plant*.—About ten days; flowers persistent.

*Fragrance*.—None detected.

*Inflorescence height*.—About 4.3 cm.

*Inflorescence diameter*.—About 5.5 cm.

*Flower buds*.—Length: About 1.8 cm. Diameter: About 1.5 cm. Shape: Oblong to narrowly obovate. Color: Developing petals; developing sepals, close to 155A.

*Flower diameter*.—About 1.4 cm.

*Flower length (height)*.—About 3.5 cm.

*Petals*.—Arrangement: Five in a single whorl; lower 60% of petal length fused. Length: About 3.1 cm. Width, base of free part of the petal: About 5 mm. Shape: Narrowly oblong. Apex: Acute. Margin: Entire. Texture, upper (inner) surface: Sparsely pubescent. Texture, lower (outer) surface: Smooth, glabrous. Color: When opening, upper (inner) surface: Close to N87A. When opening, lower (outer) surface: Close to N87A; towards the base, close to N87C. Fully opened, upper (inner) surface: Close to N87A flushed with close to N87C to N87D. Fully opened, lower (outer) surface: Close to N87A; towards the base, close to N87C and flushed with close to N87D; color does not fade with development.

*Sepals*.—Arrangement: Five in a single campanulate whorl; lower 10% of sepals fused. Length: About 1.3 cm. Width, base of free part of the sepal: About 3 mm. Shape: Lanceolate. Apex: Narrowly acute. Margin: Entire. Texture, upper and lower surfaces: Smooth; dense pubescence along the margins. Color: When developing, upper and lower surfaces: Close to 155C. Fully developed, upper and lower surfaces: Close to 155C; towards the apex, close to 157D.

*Peduncles*.—Length: About 2 mm. Diameter: About 2 mm. Aspect: Terminal inflorescences, upright; axillary inflorescences, 40° from stem axis. Strength: Strong. Texture: Slightly pubescent. Color: Close to 144C.

*Reproductive organs*.—Stamens: Quantity per flower: Five. Filament length: About 2 mm. Filament color: Close to NN155C. Anther length: About 6 mm. Anther shape: Lanceolate. Anther color: Close to 4B. Pollen amount: Moderate. Pollen color: Close to 4D. Pistils: Quantity per flower: One. Pistil length: About 2 cm. Stigma shape: Three-parted; decurrent. Stigma color: Close to 195D. Style length: About 1.8 cm. Style color: Close to 196D. Ovary color: Close to 145B to 145C.

*Seeds and fruits*.—Seed and fruit production have not been observed on plants of the new *Campanula*.

Disease & pest resistance: Plants of the new *Campanula* have not been observed to be resistant to pathogens and pests common to *Campanula* plants.

Garden performance: Plants of the new *Campanula* have exhibited good tolerance to rain and wind, are hardy to USDA Hardiness Zone 3 and have been observed to tolerate high temperatures up to 35° C.

It is claimed:

1. A new and distinct *Campanula* plant named 'Allgentitwist' as illustrated and described.

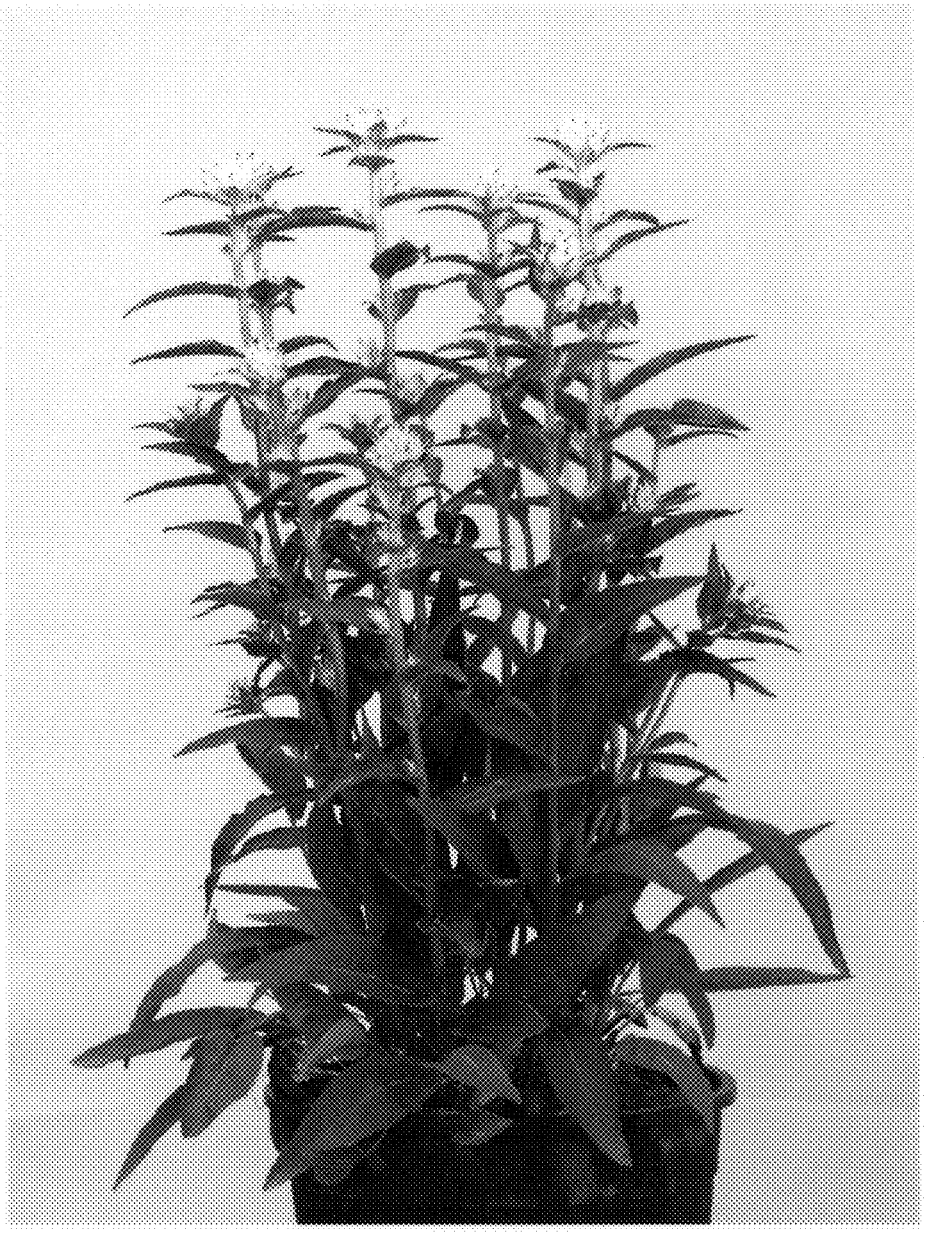

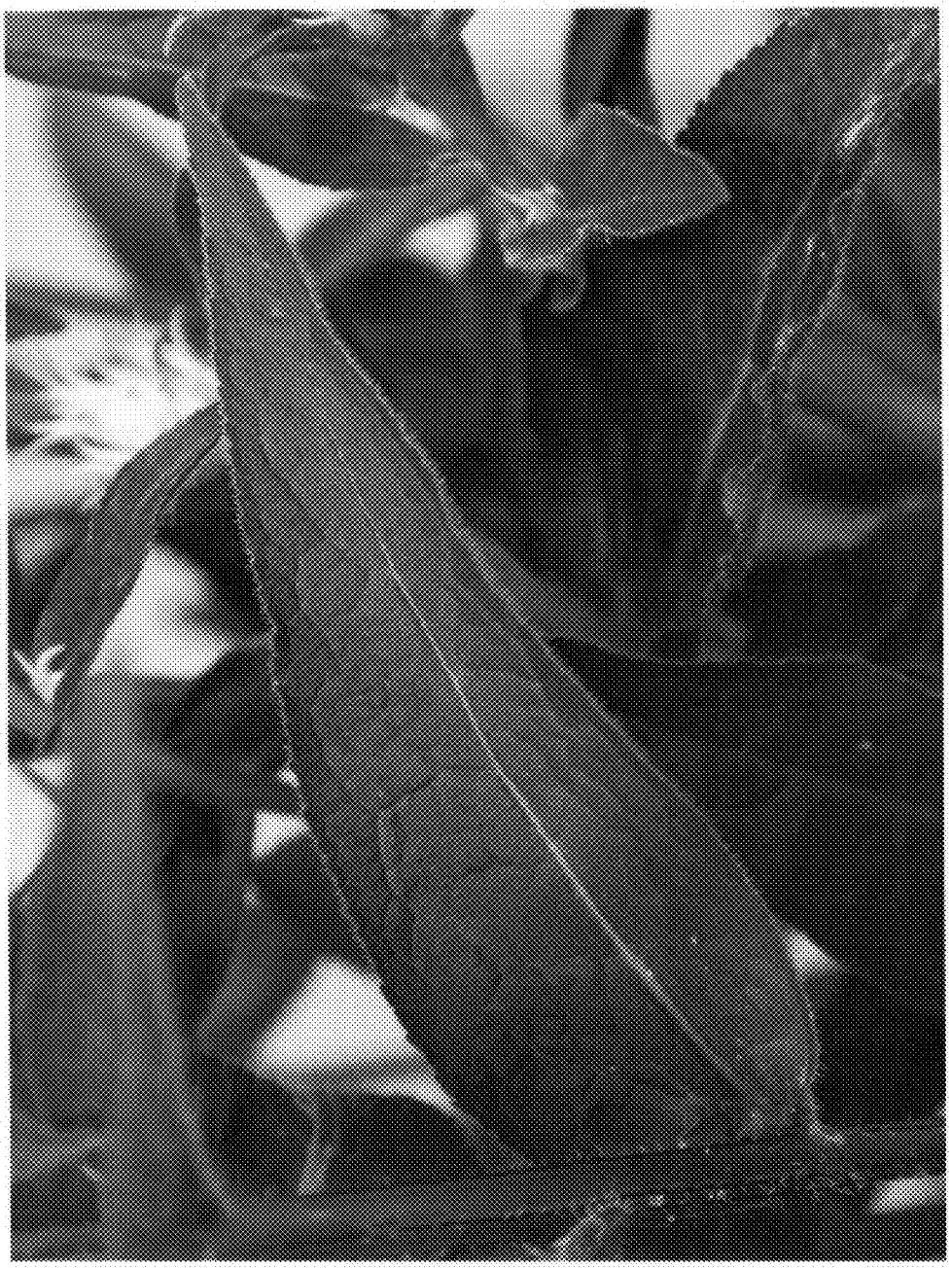

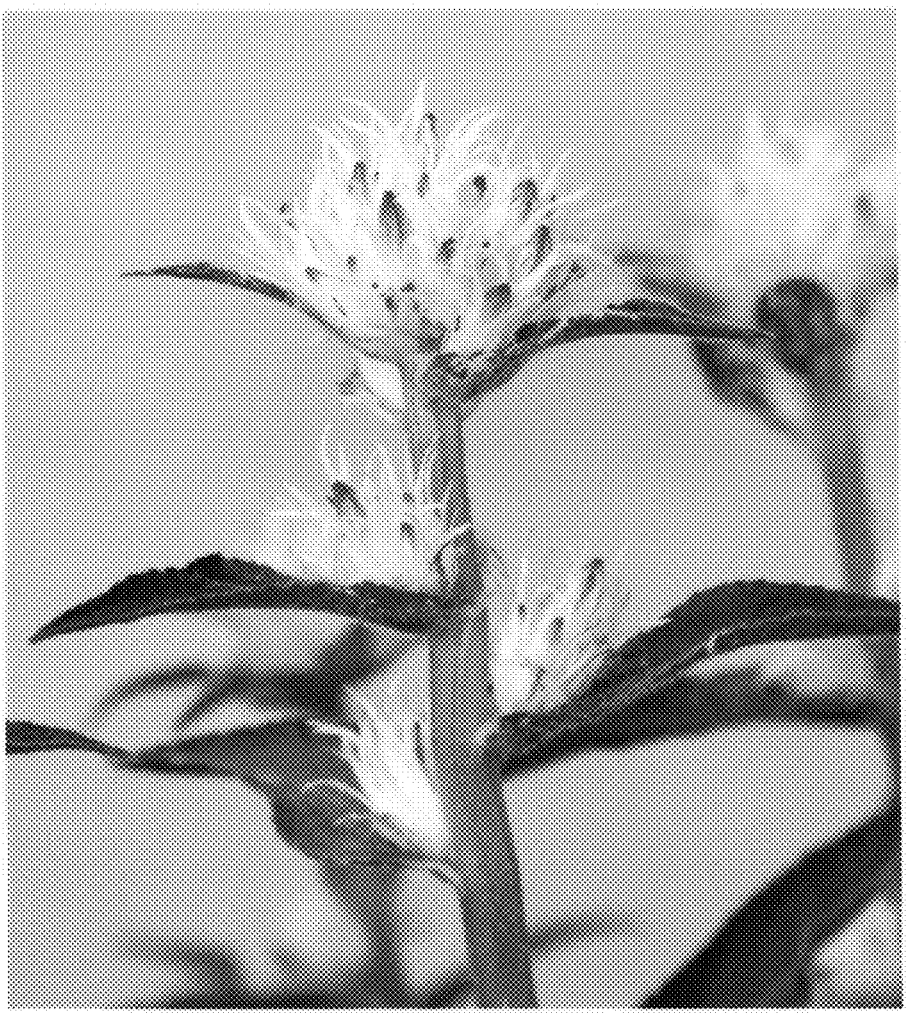

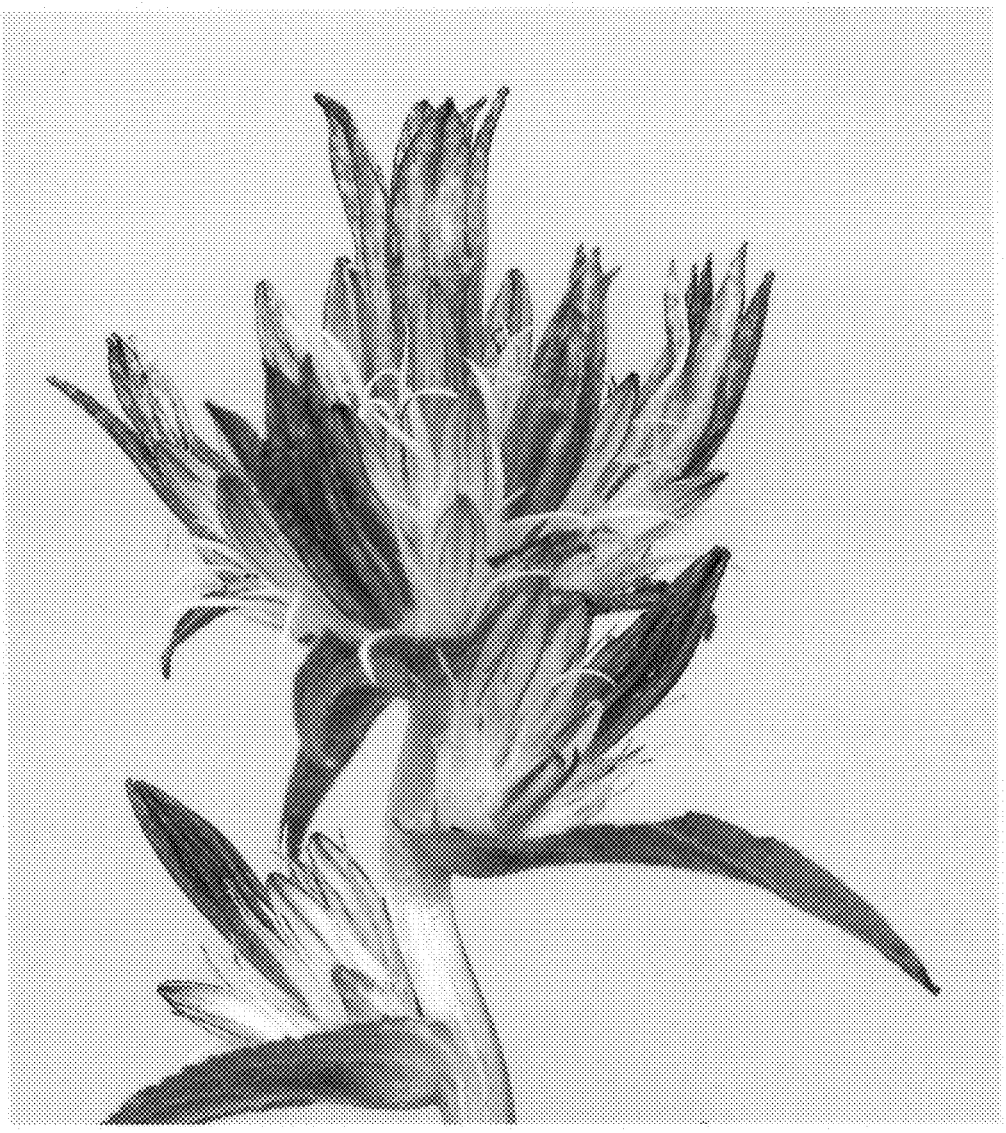

* * * * *